United States Patent [19]
Gilbert

[11] Patent Number: 5,750,574
[45] Date of Patent: May 12, 1998

[54] FLUORINATED N-ARYLMETHYLAMINO DERIVATIVES OF CYCLOBUTENE-3,4-DIONES

[75] Inventor: Adam M. Gilbert, Valley Cottage, N.Y.

[73] Assignee: American Home Products Corporation, Madison, N.J.

[21] Appl. No.: 889,163

[22] Filed: Jul. 7, 1997

Related U.S. Application Data

[60] Provisional application No. 60/021,945 Jul. 17, 1996.

[51] Int. Cl.$^6$ ............... A61K 31/135; A61K 31/165; C07C 225/20; C07C 235/82
[52] U.S. Cl. ............... 514/604; 514/605; 514/616; 514/617; 514/629; 514/655; 564/82; 564/92; 564/99; 564/182; 564/184; 564/207; 564/218; 564/306
[58] Field of Search ............... 564/306, 82, 92, 564/99, 182, 184, 207, 218; 514/604, 605, 616, 617, 629, 655

[56] References Cited

U.S. PATENT DOCUMENTS

| | | | |
|---|---|---|---|
| 4,390,701 | 6/1983 | Algieri et al. | 546/235 |
| 4,673,747 | 6/1987 | Nobara et al. | 546/334 |
| 5,240,946 | 8/1993 | Kinney et al. | 514/364 |
| 5,397,790 | 3/1995 | Butera et al. | 514/310 |
| 5,401,753 | 3/1995 | Butera et al. | 514/310 |
| 5,403,853 | 4/1995 | Butera et al. | 514/339 |
| 5,403,854 | 4/1995 | Butera et al. | 514/415 |
| 5,464,867 | 11/1995 | Antane et al. | 514/524 |
| 5,466,712 | 11/1995 | Butera et al. | 514/524 |

FOREIGN PATENT DOCUMENTS

| | | |
|---|---|---|
| 426379 | 10/1990 | European Pat. Off. |
| 496561 | 1/1992 | European Pat. Off. |
| 645385 | 3/1995 | European Pat. Off. |

OTHER PUBLICATIONS

Tietze et al., Chem. Berg., 1991, 124, 1215–1221.
Tietze et al., Bioconjugate Chem., 1991, 2, 148–153.
Ehrhardt et al., Chem. Ber., 1977, 110, 2506–2523.
Neuse et al., Liebigs Ann. Chem., 1973, 619–632.
Takeno et al. Public Patent Disclosure Bull. No. 6–92915 (Japan) 1994.
Reid et al., Liebigs Ann Chem., 1981, 402.
Kinney et al., J. Med. Chem., 192, 35, 4720.

*Primary Examiner*—Richard L. Raymond
*Attorney, Agent, or Firm*—Rebecca R. Barrett

[57] ABSTRACT

A compound of the general formula (I)

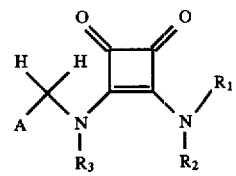

wherein $R_1$ is straight chain alkyl, branched chain alkyl, cycloalkyl, hydroxyalkyl, fluoroalkyl or polyfluoroalkyl; $R_2$ and $R_3$ are, independently, hydrogen or an acyl substituent selected from the group consisting of formyl, alkanoyl, alkenoyl, alkylsulfonyl, aroyl, arylalkenoyl, arylsulfonyl, arylalkanoyl or arylalkylsulfonyl; A is a substituted phenyl group of the following formula:

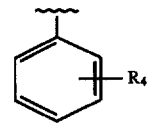

wherein $R_4$ is F, perfluoroalkyl group of 1 to 10 carbon atoms or perfluoroalkoxy of 1 to 10 carbon atoms; or a pharmaceutically acceptable salt thereof relax smooth muscles.

23 Claims, No Drawings

FLUORINATED N-ARYLMETHYLAMINO DERIVATIVES OF CYCLOBUTENE-3,4-DIONES

BACKGROUND OF INVENTION

This application claims the benefit of U.S. application Ser. No. 60/021,945, filed on Jul. 17, 1996 and is a continuation-in-part of that prior application which is incorporated by reference herein in its entirety.

Stemp et al. disclose a class of amino substituted cyclobutenedione derivatives of chromans described as having blood pressure lowering activity and bronchodilatory activity in EP-426379. Takeno et al. report a series of diaminocyclobutene-3,4-diones in Public Patent Disclosure Bulletin No. 6-92915. Our own efforts in this area have been disclosed in the following U.S. Pat. Nos.: 5,464,867, 5,466,712, 5,403,853, 5,403,854, 5,397,790, and 5,401,753. Several series of 1-amino-2-phenylalkylamino-cyclobutene-3,4-diones are reported as H-2 receptor antagonists by Algieri et al. in U.S. Pat. No. 4,390,701. Several related 1-amino-2-phenoxyalkylamino derivatives are disclosed by Nohara et al. in U.S. Pat. No. 4,673,747. Additionally, U.S. Pat. No. 5,240,946 and EP-496561 disclose diaminocyclobutene-3,4-diones useful as NMDA antagonists.

The syntheses of variously substituted 1,2-diamino-cyclobutene-3,4-diones are described in the following publications: Tietze et al., Chem. Ber. 1991, 124, 1215; Tietze et al., Bioconjugate Chem. 1991, 2, 148; Ehrhardt et al., Chem. Ber. 1977, 110, 2506, Neuse et al., Liebigs Ann. Chem. 1973, 619, Ried et al., Liebigs Ann. Chem. 1973, 619, Kinney et al., J. Med. Chem. 1992, 35, 4702.

DESCRIPTION OF THE INVENTION

The present invention relates to novel 1,2-diamino derivatives of cyclobutene 3-4-diones having pharmacological activity, to a process for their preparation, to pharmaceutical compositions containing them, and to their use in the treatment of disorders associated with smooth muscle contraction; via potassium channel modulation. Such disorders include, but are not limited to: urinary incontinence, hypertension, asthma, premature labor, irritable bowel syndrome, congestive heart failure, angina, and cerebral vascular disease.

In accordance with this invention there is provided a group of compounds represented by the formula (I):

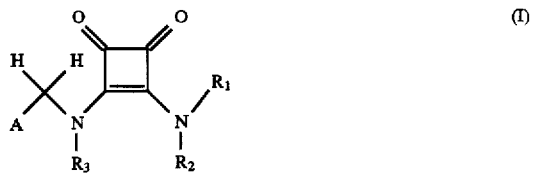

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_2$ and $R_3$ are, independently, hydrogen or an acyl substituent selected from the group consisting of formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

A is a substituted phenyl group of the following formula:

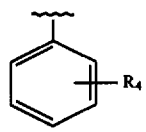

wherein:

$R_4$ is F, perfluoroalkyl group of 1 to 10 carbon atoms or perfluoroalkoxy of 1 to 10 carbon atoms;

or a pharmaceutically acceptable salt thereof.

A preferred aspect of this invention includes compounds of formula (I) wherein:

$R_1$ is straight chain alkyl of 1 to 10 carbon atoms, branched chain alkyl of 3 to 10 carbon atoms, fluoroalkyl of 1 to 10 carbon atoms or polyfluoroalkyl of 1 to 10 carbon atoms;

$R_2$ and $R_3$ are, independently, hydrogen, alkanoyl of 2 to 7 carbon atoms, alkenoyl of 3 to 7 carbon atoms, aroyl of 7 to 12 carbon atoms, or arylalkenoyl of 9 to 20 carbon atoms;

A is a substituted phenyl group of the following formula:

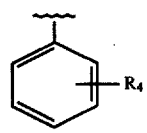

wherein:

$R_4$ is F, perfluoroalkyl group of 1 to 10 carbon atoms or perfluoroalkoxy of 1 to 10 carbon atoms;

or a pharmaceutically acceptable salt thereof.

A more preferred aspect of this invention includes compounds of formula (I) wherein:

$R_1$ is branched alkyl of 3 to 10 carbon atoms or polyfluoroalkyl of 1 to 10 carbon atoms;

$R_2$ and $R_3$ are, independently, hydrogen, alkanoyl of 2 to 7 carbon atoms or alkenoyl of 3 to 7 carbon atoms;

A is a substituted phenyl group of the following formula:

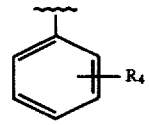

wherein:

$R_4$ is F, perfluoroalkyl group of 1 to 10 carbon atoms or perfluoroalkoxy of 1 to 10 carbon atoms;

or a pharmaceutically acceptable salt thereof.

The most preferred aspects of the present invention are:

(R)-3-(4-fluoro-benzylamino)-4-(1,2,2-trimethyl-propylamino)-cyclobut-3-ene-1,2dione or a pharmaceutically acceptable salt thereof;

(R)-3-(4-trifluoromethyl-benzylamino)-4-(1,2,2-trimethyl-propylamino)-cyclobut-3-ene-1,2-dione or a pharmaceutically acceptable salt thereof;

3-tert-butylamino-4-(4-trifluoromethoxy-benzylamino)-cyclobut-3-ene-1,2-dione or a pharmaceutically acceptable salt thereof;

3-tert-butylamino-4-(4-trifluoromethyl-benzylamino)-cyclobut-3-ene-1,2-dione or a pharmaceutically acceptable salt thereof;

3-tert-butylamino-4-(4-fluoro-benzylamino)-cyclobut-3-ene-1,2-dione or a pharmaceutically acceptable salt thereof;

(R)-3-(4-trifluoromethoxy-benzylamino)-4-(1,2,2-trimethyl-propylamino)-cyclobut-3-ene-1,2-dione or a pharmaceutically acceptable salt thereof;

3-(1,1-dimethyl-propylamino)-4-(4-fluoro-benzylamino)-cyclobut-3-ene-1,2-dione or a pharmaceutically acceptable salt thereof;

3-tert-butylamino-4-(3-fluoro-benzylamino)-cyclobut-3-ene-1,2-dione or a pharmaceutically acceptable salt thereof;

3-tert-butylamino-4-(2-fluoro-benzylamino)-cyclobut-3-ene-1,2-dione or a pharmaceutically acceptable salt thereof;

3-tert-butylamino-4-(3-trifluoromethyl-benzylamino)-cyclobut-3-ene-1,2-dione or a pharmaceutically acceptable salt thereof;

3-tert-butylamino-4-(2-trifluoromethyl-benzylamino)-cyclobut-3-ene-1,2-dione or a pharmaceutically acceptable salt thereof;

3-tert-butylamino-4-(3-trifluoromethoxy-benzylamino)-cyclobut-3-ene-1,2-dione or a pharmaceutically acceptable salt thereof;

(R)-3-(3-trifluoromethyl-benzylamino)-4-(1,2,2-trimethyl-propylamino) cyclobut-3-ene-1,2-dione or a pharmaceutically acceptable salt thereof;

(R)-3-(2-trifluoromethyl-benzylamino)-4-(1,2,2-trimethyl-propylamino) cyclobut-3-ene-1,2-dione or a pharmaceutically acceptable salt thereof;

(R)-3-(2-fluoro-benzylamino)-4-(1,2,2-trimethyl-propylamino) cyclobut-3-ene-1,2-dione or a pharmaceutically acceptable salt thereof;

(R)-3-(3-trifluoromethoxy-benzylamino)-4-(1,2,2-trimethyl-propylamino)-cyclobut3-ene-1,2-dione or a pharmaceutically acceptable salt thereof.

It is understood that the definition of the compounds of formula (I), when $R_1$, $R_2$, $R_3$, $R_4$, or $R_5$ contain asymmetric carbons, encompass all possible stereoisomers and mixtures thereof which possess the activity discussed below. In particular, it encompasses racemic modifications and any optical isomers which possess the indicated activity. Optical isomers may be obtained in pure form by standard separation techniques. The pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids.

The present invention also provides a process for the preparation of a compound of formula (I). More particularly, the compounds of formula (I) may be prepared by reacting a compound of formula (II):

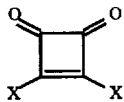

(II)

wherein X is a suitably designed leaving group such as methoxy, ethoxy, butoxy, isopropoxy, halogeno, or a similar leaving group, with a compound of formula (III):

$A_1$—$CH_2NH_2$ (III)

wherein $A_1$ is A, as defined hereinbefore or a group of atoms convertible thereto, followed by treatment with a compound of formula (IV):

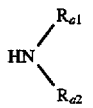

(IV)

wherein $R_{a1}$ and $R_{a2}$ are $R_1$ and $R_2$, respectively, as defined hereinbefore or a group of atoms convertible thereto in a solvent such as ethanol, acetonitrile, or the appropriate amine (IV) at elevated temperatures or room temperature. Dichloromethane can be used as a cosolvent. The order of addition of compound of formula (II) and compound of formula (IV) to compound of formula (II) may be reversed. Furthermore reaction of compound of formula (I) with the appropriate anhydride in pyridine with or without protection of the benzyl nitrogen allows for the attachment of $R_2$ and $R_3$.

As mentioned previously, the compounds of formula (I) have been found to relax smooth muscle. They are therefore useful in the treatment of disorders associated with smooth muscle contraction, disorders involving excessive smooth muscle contraction of the urinary tract (such as incontinence), or of the gastro-intestinal tract (such as irritable bowel syndrome), asthma, and hair loss. Furthermore, the compounds of formula (I) are active as potassium channel activators which render them useful for treatment of peripheral vascular disease, hypertension, congestive heart failure, stroke, anxiety, cerebral anoxia and other neurodegenerative disorders. Thus, the present invention provides a method of treating smooth muscle disorders in mammals including man, which comprises administering to the afflicted mammal an effective amount of a compound or a pharmaceutical composition of the invention.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example, parenteral administration for patient suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that use for known antihypertensive agents, diuretics and β-blocking agents.

The following examples are presented to illustrate rather than limit the scope of the invention.

EXAMPLE 1

3-(4-Fluoro-benzylamino)-4-(1,2,2-trimethyl-propylamino)-cyclobut-3-ene-1,2-dione Step 1

(R)-3-Ethoxy-4-(1,2,2-trimethyl-propylamino)-cyclobut-3-ene-1,2-dione

A solution of 3,4-diethoxy-3-cyclobutene-1,2-dione (10 g, 59 mmol) and (R)-2-amino-3,3-dimethylbutane (353 mL of a 0.2M solution in absolute ethanol, 71 mmol) was stirred at room temperature for 24 hours. Another portion of (R)-2-amino-3,3-dimethylbutane (150 mL of a 0.2M solution in absolute ethanol, 30 mmol) was added, and the resulting solution was stirred at room temperature for 24 hours. The slurry was filtered, and the filtrate concentrated under reduced pressure. The resulting solid was triturated with hexane:ethyl acetate (150:5 mL), and washed with hexane to give 9.78 g (74%) of a white solid: $^1$H NMR: (DMSO-$d_6$): δ 8.72 and 8.50 (two d, 1H, rotamers), 4.65 (m, 2H), 3.90 and 3.42 (two m, H, rotamers), 1.37 and 1.35 (two overlapping t, 2H, rotamers), 1.10 (two overlapping d, 3H, rotamers), 0.85 and 0.84 (two s, 9H, rotamers) ppm. IR(KBr): 3150, 2950, 1800, 1700 cm$^{-1}$; MS (m/z): 225 (M$^+$); Anal. Calcd. for $C_{12}H_{19}NO_3$: C, 63.98; H, 8.50; N, 6.22. Found: C, 64.33; H, 8.54; N, 6.52.

Step 2

(R)-3-(4-Fluoro-benzylamino)-4-(1,2,2-trimethyl-propylamino)-cyclobut-3-ene-1,2-dione To a solution of 100 mg (0.44 mmol) (R)-3-ethoxy-4-(1,2,2-trimethyl-propylamino)-cyclobut-3-ene-1,2-dione and 10 mL of $CH_3CN$ at room temperature, was added 55 mg (0.44 mmol) of 4-fluoro-benzylamine. The reaction mixture was heated to 80° C. for 12 hours. After cooling to room temperature and evaporation to dryness, 10 mL of $Et_2O$ was added and the mixture was filtered to give 100 mg (0.33 mmol, a 75% yield) of the (R) isomer of the title compound as a white solid. mp: 301°–303° C.; $_1$H NMR (300 MHz, DMSO-$d_6$): δ0.83–0.90 (m, 9H), 1.09–1.15 (m, 3H), 3.21–3.90 (brs, 1H), 4.71 (brm, 2H), 7.08–7.30 (m, 3H), 7.39–7.48 (m, 3H), 7.61 (brs, 1H); IR (KBr, cm$_{-1}$): 3195m, 3059w, 2967m, 2874w, 1651m, 1572s, 1511s, 1478m, 1223w; MS (ES) m/z (relative intensity): 327 (M$_+$+Na, 20), 305 (M$_+$+H, 100); Anal. Calcd. for $C_{17}H_{21}FN_2O_2$: C, 67.09; H, 6.95; N, 9.20. Found: C, 66.82; H, 7.23; N, 9.03.

EXAMPLE 2

3-(4-Trifluoromethyl-benzylamino)-4-(1,2,2-trimethyl-propylamino)-cyclobut-3-ene-1,2-dione The (R) isomer of the title compound was prepared according to the procedure for example 1-step 2 except 4-trifluoromethyl-benzylamine was used in place of 4-fluoro-benzylamine. Yield: 67%; mp: 316°–318° C.; $^1$H NMR (300 MHz, DMSO-d6): δ0.82–0.90 (m, 9H), 1.07–1.14 (m, 3H), 3.92 (brs, 1H), 4.82 (brm, 2H), 7.05–7.19 (m, 1H), 7.57 (d, J =8.2 Hz, 2H), 7.76 (d, J =8.2 Hz, 2H), 7.61 (brs, 1H); IR (KBr, cm $^{-1}$): 3196m, 3064w, 2969m, 2875w, 1649m, 1570s, 1480m, 1328m, 1127m; MS (ES) m/z (relative intensity): 377 (M$^+$+Na, 25), 355 (M$^+$+H, 100); Anal. Calcd. for $C_{18}H_{21}F_3N_2O_2$: C, 61.01; H, 5.97; N, 7.99. Found: C, 61.25; H, 6.00; N, 7.92.

EXAMPLE 3

3-tert-Butylamino-4-(4-trifluoromethoxy-benzylamino)-cyclobut-3-ene-1,2-dione

Step 1

3-Ethoxy-4-(tert-butylamino)-cyclobut-3-ene-1,2-dione

To a room temperature solution of 5.81 g (34 mmol) of 3,4-diethoxy-3-cyclobutene-1,2-dione and 50 mL of THF was added 2.9 g (34 mmol) of tert-butyl amine. After stirring at room temperature for 12 hours, the reaction mixture was evaporated to a yellow oil. Flash chromatography on silica gel, eluting with 0 to 5% $MeOH/CH_2Cl_2$ gave 6.2 g (34 mmol, a 100% yield) of the title compound as a white solid: mp: 80°–82° C.; $^1$H NMR: (300 MHz, DMSO-d6): δ1.30–1.62 (m, 12H), 4.70–4.93 (m, 2H), 5.50–6.42 (brm, 1H); IR (KBr, cm$^{-1}$): 3214w, 3144m, 3071w, 2973m, 2941m, 1794m, 1702s, 1606s, 1577s, 1500–1442brs; MS (CI) m/z (relative intensity): 198 (M$^+$H, 100); Anal. Calcd. for $C_{10}H_{15}NO_3$: C, 60.90; H, 7.67; N, 7.10. Found: C, 61.03; H, 7.66; N, 6.98.

Step 2

3-tert-Butylamino-4-(4-trifluoromethoxy-benzylamino)-cyclobut-3-ene-1,2-dione

The title compound was prepared according to the procedure for example 1-step 2 except that 3-ethoxy-4-(tert-butylamino)-cyclobut-3-ene-1,2-dione was used in place of (R)-3-ethoxy-4-(1,2,2-trimethyl-propylamino)-cyclobut-3-ene-1,2-dione and 4-trifluoromethoxy-benzylamine was used in place of 4-fluoro-benzylamine. Yield: 66%; mp: 292°–294° C.; $^1$H NMR (300 MHz, DMSO-$d_6$): δ1.36 (m, 9H), 4.73–4.79 (m 2H), 7.39 (d, J=8.0 Hz, 2H), 7.76 (d, J=8.2 Hz, 2H), 7.81 (brs, 1H), one N—H proton not seen; IR (KBr, cm$^{-1}$): 3293s, 3242s, 3061w, 2980m, 1794m, 1655s, 1569s, 1542s, 1472s, 1447s, 1280–1160brs; MS (ES) m/z (relative intensity): 365 (M$^+$+Na, 100), 343 (M$^+$+H, 75); Anal. Calcd. for $C_{16}H_{17}F_3N_2O_3$: C, 56.14; H, 5.01; N, 8.18. Found: C, 56.28; H, 5.05; N, 7.97.

EXAMPLE 4

3-tert-Butylamino-4-(4-trifluoromethyl-benzylamino)-cyclobut-3-ene-1,2-dione

The title compound was prepared according to the procedure for example 1step 2 except that 3-ethoxy-4-(tert-butylamino)-cyclobut-3-ene-1,2-dione was used in place of (R)-3-ethoxy-4-(1,2,2-trimethyl-propylamino)-cyclobut-3-ene-1,2-dione and 4-trifluoromethyl-benzylamine was used in place of 4-fluoro-benzylamine. Yield: 63%; mp: 306–308° C.; $^1$H NMR (300 MHz, DMSO-$d_6$): δ1.37 (m, 9H), 4.81–4.87 (m 2H), 7.57 (d, J=7.9 Hz, 2H), 7.76 (d, J=8.0 Hz, 2H), 7.81 (brm, 1H), one N—H proton not seen; IR (KBr, cm$^{-1}$): 3291s, 3244s, 3061w, 2980m, 1794m, 1656s, 1567s, 1540s, 1471s, 1327s, 1162s, 1127s; MS (ES) m/z (relative intensity): 349 (M$^+$+Na, 20), 327 (M$^+$+H, 100); Anal. Calcd. for $C_{16}H_{17}F_3N_2O_2$: C, 58.89; H, 5.25; N, 8.58. Found: C, 59.07; H, 5.34; N, 8.31.

EXAMPLE 5

3-tert-Butylamino-4-(4-fluoro-benzylamino)-cyclobut-3-ene-1,2-dione

The title compound was prepared according to the procedure for example 1step 2 except that 3-ethoxy-4-(tert-butylamino)-cyclobut-3-ene-1,2-dione was used in place of (R)-3-ethoxy-4-(1,2,2-trimethyl-propylamino)-cyclobut-3-ene-1,2-dione. Yield: 86%; mp: 296–298° C; $^1$H NMR (300 MHz, DMSO-$d_6$): δ1.36 (m, 9H), 4.77–4.83 (m 2H), 7.18–7.29 (m, 2H), 7.40–7.50 (m, 2H), 7.53 (s, 1H), 7.78 (brm, 1H); IR (KBr, cm$^{-1}$): 3291s, 3240s, 3069w, 2970m, 2973m, 1793m, 1654s, 1540s, 1511s, 1471s, 1455s, 1219s; MS (CI) m/z (relative intensity): 277 (M++H, 100); Anal. Calcd. for $C_{15}H_{17}FN_2O_2$: C, 65.20; H, 6.20; N, 10.14. Found: C, 65.19; H, 6.25; N, 10.06.

EXAMPLE 6

3-(4-Trifluoromethoxy-benzylamino)-4-(1,2,2-trimethyl-propylamino) cyclobut-3-ene-1,2-dione The (R) isomer of the title compound was prepared according to the procedure for example 1-step 2 except that 4-trifluromethyl-benzylamine was used in place of 4-fluoro-benzylamine. Yield: 61%; mp: 289–291° C.; $^1$H NMR (300 MHz, DMSOd-$d_6$): δ 0.83–0.88 (m, 9H), 1.08–1.14 (m, 3H), 3.91 (brs, 1H), 4.71–4.81 (m, 2H), 7.39 (d, J=8.1 Hz, 2H), 7.48 (d, J=8.1 Hz, 2H), 7.65 (brs, 1H), one NH proton not seen; IR (KBr, cm$^{-1}$): 3196m, 3064w, 2969m, 1796w, 1648m, 1575s, 1511s, 1480s, 1347m, 1264m, 1162s; MS (ES) m/z (relative intensity): 393 (M$^+$+Na, 20), 371 (M$^+$+H, 100); Anal. Calcd. for $C_{18}H_{21}F_3N_2O_3$: C, 58.37; H, 5.72; N, 7.56. Found: C, 59.20; H, 6.01; N, 7.56.

EXAMPLE 7

3-(1,1-Dimethyl-propylamino)-4-(4-fluoro-benzylamino)-cyclobut-3-ene-1,2 dione Step 1

3-Ethoxy-4-(1,1-dimethyl-propylamino)-cyclobut-3-ene-1,2-dione

To a room temperature solution of 4.9 g (29 mmol) of 3,4-diethoxy-3-cyclobutene-1,2-dione and 50 mL of THF was added 2.5 g (34 mmol) of 1,1-dimethyl-propylamine. After stirring at room temperature overnight, the reaction mixture was evaporated to a yellow oil. Trituration with $Et_2O$ and filtration gave 6.2 g (20 mmol, a 100% yield) of the title compound as a white solid: mp: 78–80° C.; $^1$H NMR: (300 MHz, DMSO-$d_6$): δ 0.91 and 1.47 (t, J=7.5 Hz, 3H, rotamers), 1.36–1.97 (m, 6H), 4.70–4.92 (m, 2H), 5.41 and 5.99 (brs, 1H, rotamers); IR (KBr, cm$^{-1}$H): 3252w, 3181w, 3067w, 2968m, 2887m, 1788m, 1695s, 1603s, 1578s, 1500–1434brs, 1343s; MS (CI) m/z (relative intensity): 212 (M$^+$+H, 100); Anal. Calcd. for $C_{10}H_{15}NO_3$: C 62.54; H 8.11; N 6.63. Found: C, 62.54; H, 8.12; N, 6.52.

Step 2

3-(1,1-Dimethyl-propylamino)-4-(4-fluoro-benzylamino)-cyclobut-3-ene-1,2 dione

The title compound was prepared according to the procedure for example 1-step 2 except that 3-ethoxy-4-(1,1-dimethyl-propylamino)-cyclobut-3-ene-1,2-dione was used in place of (R)-3-ethoxy-4-(1,2,2-trimethyl-propylamino)-cyclobut-3-ene-1,2-dione. Yield: 72%; mp: 255–257° C.; $^1$H NMR (300 MHz, DMSO-$d_6$): δ 0.82 (t, J=7.5 Hz, 3H), 1.30 (s, 6H), 1.67 (q, J=7.5 Hz, 2H), 4.69–4.74 (m 2H), 7.19–7.31 (m, 2H), 7.37–7.55 (m, 3H), 7.80 (brs, 1H); IR (KBr, cm$^{-1}$): 3239m, 3069w, 2972w, 2882w, 1792w, 1652m, 1571s, 1537s, 1511m, 1468w; MS (ES) m/z (relative intensity): 313 (M$^+$+Na, 30), 291 (M$^+$+H, 100); Anal. Calcd. for $C_{16}H_{19}FN_2O_2$: C, 66.19; H, 6.60; N, 9.65. Found: C, 66.25; H, 6.72; N, 9.51.

EXAMPLE 8

3-tert-Butylamino-4-(3-fluoro-benzylamino)-cyclobut-3-ene-1,2-dione

The title compound was prepared according to the procedure for example 1-step 2 except that 3-ethoxy-4-(tert-butylamino)-cyclobut-3-ene-1,2-dione was used in place of (R)-3-ethoxy-4-(1,2,2-trimethyl-propylamino)-cyclobut-3-ene-1,2-dione and 3-trifluoro-benzylamine was used in place of 4-fluoro-benzylamine. Yield: 75%; mp: 295–297° C.; $^1$H NMR (300 MHz, DMSO-$d_6$): δ 1.37 (m, 9H), 4.72–4.79 (m 2H), 7.11–7.26 (m, 3H), 7.40–7.49 (m, 1H), 7.54 (brs, 1H), 7.75–7.84 (brm, 1H); IR (KBr, cm$^-$): 3236s, 3091w, 2971m, 2937m, 1794m, 1654s, 1571s, 1536s, 1470s, 1444s, 1370m, 1248m, 1216m; MS (ES) m/z (relative intensity): 299 (M$^+$+Na, 15), 277 (M$^+$+H, 100); Anal. Calcd. for $C_{15}H_{17}FN_2O$: C, 65.20; H, 6.20; N, 10.14. Found: C, 65.09; H, 6.28; N, 10.19.

EXAMPLE 9

3-tert-Butylamino-4-(2-fluoro-benzylamino)-cyclobut-3-ene-1,2-dione

The title compound was prepared according to the procedure for example 1-step 2 except that 3-ethoxy-4-(tert-butylamino)-cyclobut-3-ene-1,2-dione was used in place of (R)-3-ethoxy-4-(1,2,2-trimethyl-propylamino)-cyclobut-3-ene-1,2-dione and 2-trifluromethoxy-benzylamine was used in place of 4-fluoro-benzylamine. Yield: 73%; mp: 260–262° C.; $^{1\,H\,NMR}$ (300 MHz, DMSO-$d_6$): δ 1.36 (m, 9H), 4.75–4.81 (m 2H), 7.20–7.30 (m, 2H), 7.35–7.46 (m, 2H), 7.53 (brs, 1H), 7.72–7.80 (brm, 1H); IR (KBr, cm$^{-1}$): 3221m, 3048w, 2973m, 1793m, 1653s, 1570s, 1537s, 1470–1445brs, 1231m, 1217m; MS (ES) m/z (relative intensity): 299 (M$^+$+Na, 10), 277 (M$^+$+H, 100); Anal. Calcd. for $C_{15}H_{17}FN_2O_2$: C, 65.20; H, 6.20; N, 10.14. Found: C, 64.99; H, 6.09; N, 9.99.

EXAMPLE 10

3-tert-Butylamino-4-(3-trifluoromethyl-benzylamino)-cyclobut-3-ene-1,2-dione The title compound was prepared according to the procedure for example 1-step 2 except that 3-ethoxy-4-(tert-butylamino)-cyclobut-3-ene-1,2-dione was used in place of (R)-3-ethoxy-4-(1,2,2-trimethyl-propylamino)-cyclobut-3-ene-1,2-dione and 3-trifluoromethyl-benzylamine was used in place of 4-fluoro-benzylamine. Yield: 73%; mp: 237–239° C.; $^{1\,H\,NMR}$ (300 MHz, DMSO-$d_6$) δ 1.36 (s, 9H), 4.81–4.87 (m, 2H), 7.57 (s, 1H), 7.60–7.77 (m, 4H), 7.82 (brm, 1H); IR (KBr, cm$^{-1}$): 3233m, 3059w, 2973w, 1793w, 1653s, 1571s, 1540s, 1471m, 1447m, 1354m, 1166m, 1127m; MS (CI) m/z (relative intensity): 327 (M$^+$+H, 80); Anal. Calcd. for $C_{16}H_{17}F_3N_2O_2$: C, 58.89; H, 5.25; N, 8.58. Found: C, 58.99; H, 5.23; N, 8.47.

EXAMPLE 11

3-tert-Butylamino-4-(2-trifluoromethyl-benzylamino)-cyclobut-3-ene-1,2-dione The title compound was prepared according to the procedure for example 1-step 2 except that 3-ethoxy-4-(tert-butylamino)-cyclobut-3-ene-1,2-dione was used in place of (R)-3-ethoxy-4-(1,2,2-trimethyl-propylamino)-cyclobut-3-ene-1,2-dione and 2-trifluoromethyl-benzylamine was used in place of 4-fluoro-benzylamine. Yield: 73%; mp: 237–239° C.; $^1$H NMR (300 MHz, DMSO-$d_6$) δ 1.37 (m, 9H), 4.81–4.88 (m 2H), 7.56–7.61 (m, 2H), 7.63–7.83 (m, 4H); IR (KBr, cm$^{-1}$): 3299m, 3224m, 3040w, 2976w, 2940w, 1796m, 1670m, 1650m, 1576s, 1534s, 1468s, 1315s, 1216–1127brm; MS (ES) m/z (relative intensity): 349 (M$^+$+Na, 20), 327 (M$^+$+H, 100); Anal. Calcd. for $C_{16}H_{17}F_3N_2O_2$: C, 58.89; H, 5.25; N, 8.58. Found: C, 58.84; H, 5.28; N, 8.54.

EXAMPLE 12

3-tert-Butylamino-4-(3-trifluoromethoxy-benzylamino)-cyclobut-3-ene-1,2-dione The title compound was prepared according to the procedure for example 1-step 2 except that 3-ethoxy-4-(tert-butylamino)-cyclobut-3-ene-1,2-dione was used in place of using (R)-3-ethoxy-4-(1,2,2-trimethyl-propylamino)-cyclobut-3-ene-1,2-dione and 3-trifluoromethoxy-benzylamine was used in place of 4-fluorobenzylamine. Yield: 66%; mp: 210–212° C.; $^1$H NMR (300 MHz, DMSO-$d_6$): δ 1.36 (m, 9H), 4.76–4.81 (m 2H), 7.32–7.43 (m, 3H), 7.50–7.60 (m, 2H), 7.76–7.84 (brm, 1H); IR (KBr, cm$^{-1}$): 3295m, 3239m, 3063w, 2973m, 1794m, 1655s, 1569s, 1542s, 1471s, 1446s, 1259–1168brs; MS (ES) m/z (relative intensity): 365 (M$^+$+Na, 50), 343 (M$^+$+H, 100); Anal. Calcd. for $C_{16}H_{17}F_3N_2O_3$: C, 56.14; H, 5.01; N, 8.18. Found: C, 55.91; H, 4.70; N, 7.99.

EXAMPLE 13

3-(3-Trifluoromethyl-benzylamino)-4-(1,2,2-trimethyl-propylamino) cyclobut-3-ene-1,2-dione The (R) isomer of the title compound was prepared according to the procedure for example 1-step 2 except that 3-trifluromethyl-benzylamine was used in place of 4-fluoro-benzylamine. Yield: 76%; mp: 236°–238° C.; $^1$H NMR (300 MHz, DMSO-$d_6$): δ 0.83–0.90 (m, 9H), 1.09–1.15 (m, 3H), 3.88–3.96 (m, 1H), 4.75–4.90 (m, 2H), 7.15–7.38 (m, 1H), 7.59–7.82 (m, 5H); IR (KBr, cm$^{-1}$): 3201m, 3061w, 2969m, 2876w, 1790w, 1649m, 1569brs, 1480m, 1329s, 1167m, 1126m; MS (CI) m/z (relative intensity): 355 (M$^+$+H, 20); Anal. Calcd. for $C_{18}H_{21}F_3N_2O_2$: C, 61.01; H, 5.97; N, 87.90. Found: C, 61.41; H, 5.94; N, 7.96.

EXAMPLE 14

3-(2-Trifluoromethyl-benzylamino)-4-(1,2,2-trimethyl-propylamino) cyclobut-3-ene-1,2-dione The (R) isomer of the title compound was prepared according to the procedure for example 1-step 2 except that 2-trifluromethyl-benzylamine was used in place of 4-fluoro-benzylamine. Yield: 76%; mp: 216°–218° C.; $^1$H NMR (300 MHz, DMSO-$d_6$): δ 0.83–0.90 (m, 9H), 1.10–1.16 (m, 3H), 3.88–3.97 (m, 1H), 4.80–4.91 (m, 2H), 7.17–7.40 (m, 1H), 7.59–7.82 (m, 5H); IR (KBr, cm$^{-1}$): 3210m, 3066w, 2967m, 2875w, 1664m, 1586s, 1541s, 1476m, 1315s, 1165m, 1122m; MS (CI) m/z (relative intensity): 355 (M$^+$+H, 100); Anal. Calcd. for $C_{18}H_{21}F_3N_2O_2$: C, 61.01; H, 5.97; N, 7.90. Found: C, 61.23; H, 5.69; N, 7.91.

EXAMPLE 15

3-(2-Fluoro-benzylamino)-4-(1,2,2-trimethyl-propylamino) cyclobut-3-ene-1,2-dione The (R) isomer of the title compound was prepared according to the procedure for example 1-step 2 except that 2-fluoro-benzylamine was used in place of 4-fluoro-benzylamine. Yield: 66%; mp: 275°–277° C.; $^1$H NMR (300 MHz, DMSO-$d_6$): δ 0.84–0.9(m, 9H), 1.08–1.14 (m, 3H), 3.85–3.96 (m, 1H), 4.70–4.90 (m, 2H), 7.15–7.32 (m, 3H), 7.37–7.55 (m, 2H), 7.60–7.76 (m, 1H); IR (KBr, cm$^{-1}$): 3193m, 3065w, 2967m, 2874m, 1648m, 1574s, 1545s, 1489–1421brm, 1368w; MS (ES) m/z (relative intensity): 327 (M$^+$+Na, 20), 305 (M$^+$+H, 100); Anal. Calcd. for $C_{17}H_{21}FN_2O_2$: C, 67.09; H, 6.95; N, 9.20. Found: C, 66.79; H, 7.16; N, 9.08.

EXAMPLE 16

3-(3-Trifluoromethoxy-benzylamino)-4-(1,2,2-trimethyl-propylamino) cyclobut-3-ene-1,2-dione The (R) isomer of the title compound was prepared according to the procedure for example 1-step 2 except that 3-trifluoromethoxy-benzylamine was used in place of 4-fluoro-benzylamine. Yield: 60%; mp: 236°–238° C.; $^1$H NMR (300 MHz, DMSO-$d_6$): δ 0.84–0.90 (m, 9H), 1.10–1.15 (m, 3H), 3.88–3.97 (m, 1H), 4.73–4.85 (m, 2H), 7.15–7.45 (m, 4H), 7.50–7.58 (m, 1H), 7.62–7.77 (m, 1H); IR (KBr, cm$^{-1}$): 3201m, 3065w, 2968m, 2876w, 1648m, 1567s, 1481m, 1449m, 1262m, 1216m; MS (ES) m/z (relative intensity): 393 (M$^+$+Na, 25), 371 (M$^+$+H, 100); Anal. Calcd. for $C_{18}H_{21}F_3N_2O_3$: C, 58.37; H, 5.72; N, 7.56. Found: C, 59.02; H, 5.99; N, 7.57.

The smooth muscle relaxing activity of the compounds of this invention was established in accordance with standard pharmaceutically accepted test procedures with representative compounds as follows:

Sprague-Dawley rats (150–200 g) are rendered unconscious by $CO_2$ asphyxiation and then euthanized by cervical dislocation. The bladder is removed into warm (37° C.) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; 2/5% $CO_2$; pH 7.4 The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 μM carbachol. The carbachol is then washed out and the tissue allowed to relax to its resting level of activity. Following a further 30 min. period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity ($IC_{50}$ concentration) and is calculated from this concentration-response curve. The maximum percentage inhibition of contractile activity evoked by a test compound is also recorded for concentrations of test compound less than or equal to 30 μM.

The results of this study are shown in Table I.

TABLE I

| Inhibition of Contractions in Isolated Rat Bladder Strips | | |
|---|---|---|
| Compound | n | $IC_{50}$ (μM) |
| Example 1 | 3 | 0.76 ± 0.46 |
| Example 2 | 4 | 6.5 ± 1.9 |
| Example 3 | 1 | 16.2ª |
| Example 4 | 3 | 6.5 ± 0.87 |
| Example 5 | 4 | 1.5 ± 0.32 |
| Example 6 | 1 | 20.4ª |
| Example 7 | 4 | 0.36 ± 0.14 |
| Example 8 | 3 | 2.4 ± 0.36 |
| Example 9 | 4 | 2.08 ± 0.25 |
| Example 10 | 4 | 7.9 ± 2.7 |

TABLE I-continued

Inhibition of Contractions in Isolated Rat Bladder Strips

| Compound | n | $IC_{50}$ (μM) |
|---|---|---|
| Example 11 | 4 | 2.3 ± 0.51 |
| Example 12 | 3 | 13.6 ± 3.3 |
| Example 13 | 4 | 40.1[a] |
| Example 14 | 2 | 20.4 ± 7.8 |
| Example 15 | 4 | 1.23 ± 0.22 |
| Example 16 | 1 | 10[a] |

[a]Percent inhibition at 30 μM

In addition, we tested the ability of compounds to inhibit the hyperactivity of hypertrophied bladder (detrussor) smooth muscle in conscious female rats with hypertrophied bladders and thereby alleviate urinary incontinence in rats according to the following protocol described by Malmgren (A. Malmgren, K. E. Andersson, C. Sjogren, P. O. Andersson, Effects of pinacidil and Cromakalim (BRL 34915) on Bladder Function in Rats with Detrusor Instability, *J. Urol.* 142:1134, 1989.):

Female Sprague-Dawley rats, ranging in weight from 190–210 g are used. Up to 25 animals are prepared each time. After development of bladder hypertrophy 4–8 animals are used per test.

Compounds are dissolved in PEG-200 and administered by gastric gavage or intraveneously in a volume of 5 ml/kg. For primary screening all drugs are administered at the arbitrary dose of 10 mg/kg p.o. to groups of 4 rats.

The animals are anesthetized with halothane. Through a midline incision the bladder and urethra are exposed and a ligature of 4-0 silk is tied around the proximal urethra in the presence of a stainless steel rod (1 mm diameter) to produce a partial occlusion. The rod is then removed. The abdominal region is closed using surgical staples and each rat receives 150,000 units of bicillin C–R. The animals ar allowed six weeks to develop sufficient bladder hypertrophy. After six weeks, the ligature is removed under halothane anesthesia and a catheter (PE 60) with a cuff is placed in the dome of the bladder and secured with a purse string suture. The catheter is tunneled under the skin and exteriorized through an opening in the back of the neck. The abdominal incision is sutured and the free end of the catheter sealed. In order to prevent infections the rats receive an injection of bicillin C–R (150000 units/rat). Two days later the animals are used in cystometrical evaluations. The animals are placed in the metabolic cages and the catheter is attached (using a "T" connector) to a Statham pressure transducer (Model P23Db) and to a Harvard infusion pump. A plastic beaker attached to a force displacement transducer (Grass FT03) is placed under the rat's cage to collect and record urine volume. Animals are allowed 15–30 min to rest before the saline infusion (20 ml/hr for 20 minutes) is started for the first cystometry period. Two hours after the first cystometry period, the rats are dosed with the vehicle or the test compound and one hour later a second cystometry is performed.

The following urodynamic variables are recorded:

Basal bladder pressure =the lowest bladder pressure during cystometry

Threshold pressure =bladder pressure immediately prior to micturition

Micturition volume =volume expelled

Micturition pressure =peak pressure during voiding

Spontaneous activity =mean amplitude of bladder pressure fluctuations during filling Presentation of results:

The mean value of each variable is calculated before and after compound administration. For each compound the changes in the variables measured are compared to the values obtained before treatment and expressed as percent inhibition. The data are also subjected to 2-way analysis of variance to determine significant (p<0.05) changes in the variable measured.

Criteria for Activity:

The most characteristic finding in this rat model is spontaneous bladder contractions which develop during filling. The compounds which inhibit spontaneous contractions by at least 50% at 10 mg/kg p.o. or i.v. (arbitrary chosen dose) are considered active.

The results of this study are shown in Table II.

TABLE II

Inhibition of Spontaneous Contractions In Vivo

| Compound | # of animals | dose mg/kg (p.o.) | % Red (F)[c] | % Ampl[d] |
|---|---|---|---|---|
| Example 1 | 4 | 3 mg/kg | 3 ± 25 | −64 ± 3 |
| Example 7 | 4 | 3 mg/kg | 67 ± 2 | −3 ± 35 |

[c]Percent reduction in the total number of spontaneous contractions in the hypertrophied rat bladder model
[d]Percent change in the amplitude of spontaneous contractions in the hypertrophied rat bladder model Hence, the compounds of this invention have a pronounced effect on smooth muscle contractility and are useful in the treatment of urinary incontinence, irritable bladder and bowel disease, asthma, hypertension, stroke, and similar diseases as mentioned above, which are amenable to treatment with potassium channel activating compounds by administration, orally, parenterally or by aspiration to a patient in need thereof.

I claim:

1. A compound of the general formula (I)

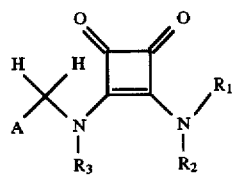

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_2$ and $R_3$ are, independently, hydrogen or an acyl substituent selected from the group consisting of formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

13

A is a substituted phenyl group of the following formula:

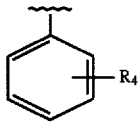

wherein:

$R_4$ is F, perfluoroalkyl group of 1 to 10 carbon atoms or perfluoroalkoxy of 1 to 10 carbon atoms;

or a pharmaceutically acceptable salt thereof.

2. A compound according to claim 1 of formula (I) wherein:

$R_1$ is straight chain alkyl of 1 to 10 carbon atoms, branched chain alkyl of 3 to 10 carbon atoms, fluoroalkyl of 1 to 10 carbon atoms or polyfluoroalkyl of 1 to 10 carbon atoms;

$R_2$ and $R_3$ are, independently, hydrogen, alkanoyl of 2 to 7 carbon atoms, alkenoyl of 3 to 7 carbon atoms, aroyl of 7 to 12 carbon atoms, or arylalkenoyl of 9 to 20 carbon atoms;

A is a substituted phenyl group of the following formula:

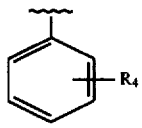

wherein:

$R_4$ is F, perfluoroalkyl group of 1 to 10 carbon atoms or perfluoroalkoxy of 1 to 10 carbon atoms;

or a pharmaceutically acceptable salt thereof.

3. A compound according to claim 1 of formula (I) wherein:

$R_1$ is branched alkyl of 3 to 10 carbon atoms or polyfluoroalkyl of 1 to 10 carbon atoms;

$R_2$ and $R_3$ are, independently, hydrogen, alkanoyl of 2 to 7 carbon atoms or alkenoyl of 3 to 7 carbon atoms;

A is a substituted phenyl group of the following formula:

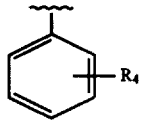

wherein:

$R_4$ is F, perfluoroalkyl group of 1 to 10 carbon atoms or perfluoroalkoxy of 1 to 10 carbon atoms;

or a pharmaceutically acceptable salt thereof.

4. The compound of claim 1 which is 3-(4-fluoro-benzylamino)-4-(1,2,2-trimethyl-propylamino)-cyclobut-3-ene-1,2-dione or a pharmaceutically acceptable salt thereof.

5. The compound of claim 1 which is 3-(4-trifluoromethyl-benzylamino)-4(1,2,2-trimethyl-propylamino)-cyclobut-3-ene-1,2-dione or a pharmaceutically acceptable salt thereof.

6. The compound of claim 1 which is 3-tert-butylamino-4-(4-trifluoromethoxy-benzylamino)-cyclobut-3-ene-1,2-dione or a pharmaceutically acceptable salt thereof.

7. The compound of claim 1 which is 3-tert-butylamino-4-(4-trifluoromethyl-benzylamino)-cyclobut-3-ene-1,2-dione or a pharmaceutically acceptable salt thereof.

14

8. The compound of claim 1 which is 3-tert-butylamino-4-(4-fluoro-benzylamino)-cyclobut-3-ene-1,2-dione or a pharmaceutically acceptable salt thereof.

9. The compound of claim 1 which is 3-(4-trifluoromethoxy-benzylamino)-4-(1,2,2-trimethyl-propylamino)-cyclobut-3-ene-1,2-dione or a pharmaceutically acceptable salt thereof.

10. The compound of claim 1 which is 3-(1,1-dimethyl-propylamino)-4-(4-fluoro-benzylamino)-cyclobut-3-ene-1,2-dione or a pharmaceutically acceptable salt thereof.

11. The compound of claim 1 which is 3-tert-butylamino-4-(3-fluorobenzyl-amino)-cyclobut-3-ene-1,2-dione or a pharmaceutically acceptable salt thereof.

12. The compound of claim 1 which is 3-tert-butylamino-4-(2-fluoro-benzylamino)-cyclobut-3-ene-1,2-dione or a pharmaceutically acceptable salt thereof.

13. The compound of claim 1 which is 3-tert-butylamino-4-(3-trifluoromethyl-benzylamino)-cyclobut-3-ene-1,2-dione or a pharmaceutically acceptable salt thereof.

14. The compound of claim 1 which is 3-tert-butylamino-4-(2-trifluoromethyl-benzylamino)-cyclobut-3-ene-1,2-dione or a pharmaceutically acceptable salt thereof.

15. The compound of claim 1 which is 3-tert-butylamino-4-(3-trifluoromethoxy-benzylamino)-cyclobut-3-ene-1,2-dione or a pharmaceutically acceptable salt thereof.

16. The compound of claim 1 which is 3-(3-trifluoromethyl-benzylamino)-4-(1,2,2-trimethyl-propylamino)cyclobut-3-ene-1,2-dione or a pharmaceutically acceptable salt thereof.

17. The compound of claim 1 which is 3-(2-trifluoromethyl-benzylamino)-4-(1,2,2-trimethyl-propylamino)cyclobut-3-ene-1,2-dione or a pharmaceutically acceptable salt thereof.

18. The compound of claim 1 which is 3-(2-fluoro-benzylamino)-4-(1,2,2trimethyl-propylamino)cyclobut-3-ene-1,2-dione or a pharmaceutically acceptable salt thereof.

19. The compound of claim 1 which is 3-(3-trifluoromethoxy-benzylamino)-4-(1,2,2-trimethyl-propylamino)-cyclobut-3-ene-1,2-dione or a pharmaceutically acceptable salt thereof.

20. A pharmaceutical composition of matter comprising a compound of the formula:

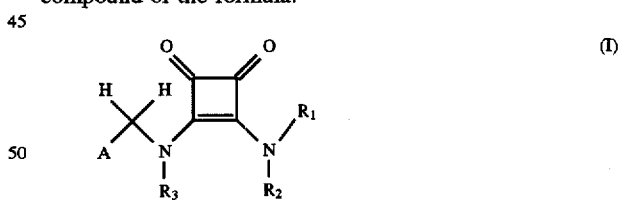

(I)

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_2$ and $R_3$ are, independently, hydrogen or an acyl substituent selected from the group consisting of formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

A is a substituted phenyl group of the following formula:

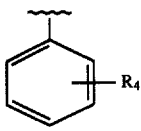

wherein:

$R_4$ is F, perfluoroalkyl group of 1 to 10 carbon atoms or perfluoroalkoxy of 1 to 10 carbon atoms;

or a pharmaceutically acceptable salt thereof and a pharmaceutically acceptable carrier therefor.

21. A method for reducing the adverse effects of smooth muscle contractions which comprises administering, orally or parenterally, to a patient in need thereof, a compound of the formula:

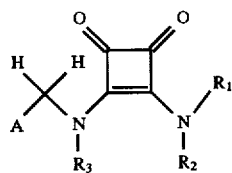

(I)

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_2$ and $R_3$ are, independently, hydrogen or an acyl substituent selected from the group consisting of formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

A is a substituted phenyl group of the following formula:

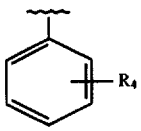

wherein:

$R_4$ is F, perfluoroalkyl group of 1 to 10 carbon atoms or perfluoroalkoxy of 1 to 10 carbon atoms;

or a pharmaceutically acceptable salt thereof.

22. The method of claim 23 in which the smooth muscle adversely contracting causes urinary incontinence.

23. The method of claim 23 in which the smooth muscle adversely contracting causes irritable bowel syndrome.

* * * * *